United States Patent [19]
Loughner

[11] 3,931,646
[45] Jan. 13, 1976

[54] DOUBLE LENS GOGGLE
[75] Inventor: Larry Gordon Loughner, Andover, Mass.
[73] Assignee: American Optical Corporation, Southbridge, Mass.
[22] Filed: June 26, 1974
[21] Appl. No.: 483,206

[52] U.S. Cl. ................................. 2/14 V; 2/14 XS
[51] Int. Cl.[2] ............................................ A61F 9/02
[58] Field of Search...... 2/14 XS, 14 V, 14 K, 14 R, 2/14 N, 8

[56] References Cited
UNITED STATES PATENTS
| | | | |
|---|---|---|---|
| 1,916,678 | 7/1933 | Malcom | 2/14 XS X |
| 3,173,147 | 3/1965 | Gross et al. | 2/14 V |
| 3,373,444 | 3/1968 | Militello | 2/8 X |
| 3,505,680 | 4/1970 | Ring | 2/14 K |

FOREIGN PATENTS OR APPLICATIONS
201,777   7/1958   Austria ............................. 2/14 XS Primary Examiner—Werner H. Schroeder
Assistant Examiner—Peter Nerbun
Attorney, Agent, or Firm—H. R. Berkenstock, Jr.; William C. Nealon

[57] ABSTRACT

A double lens headband supported sports goggle system having a fixed main lens and an outer auxiliary lens, the latter being pivotally harnessed to the headband for selective use in conjunction with the main lens or for storage thereabove or below against a wearer's head without detachment from the system.

5 Claims, 3 Drawing Figures

U.S. Patent  Jan. 13, 1976  3,931,646
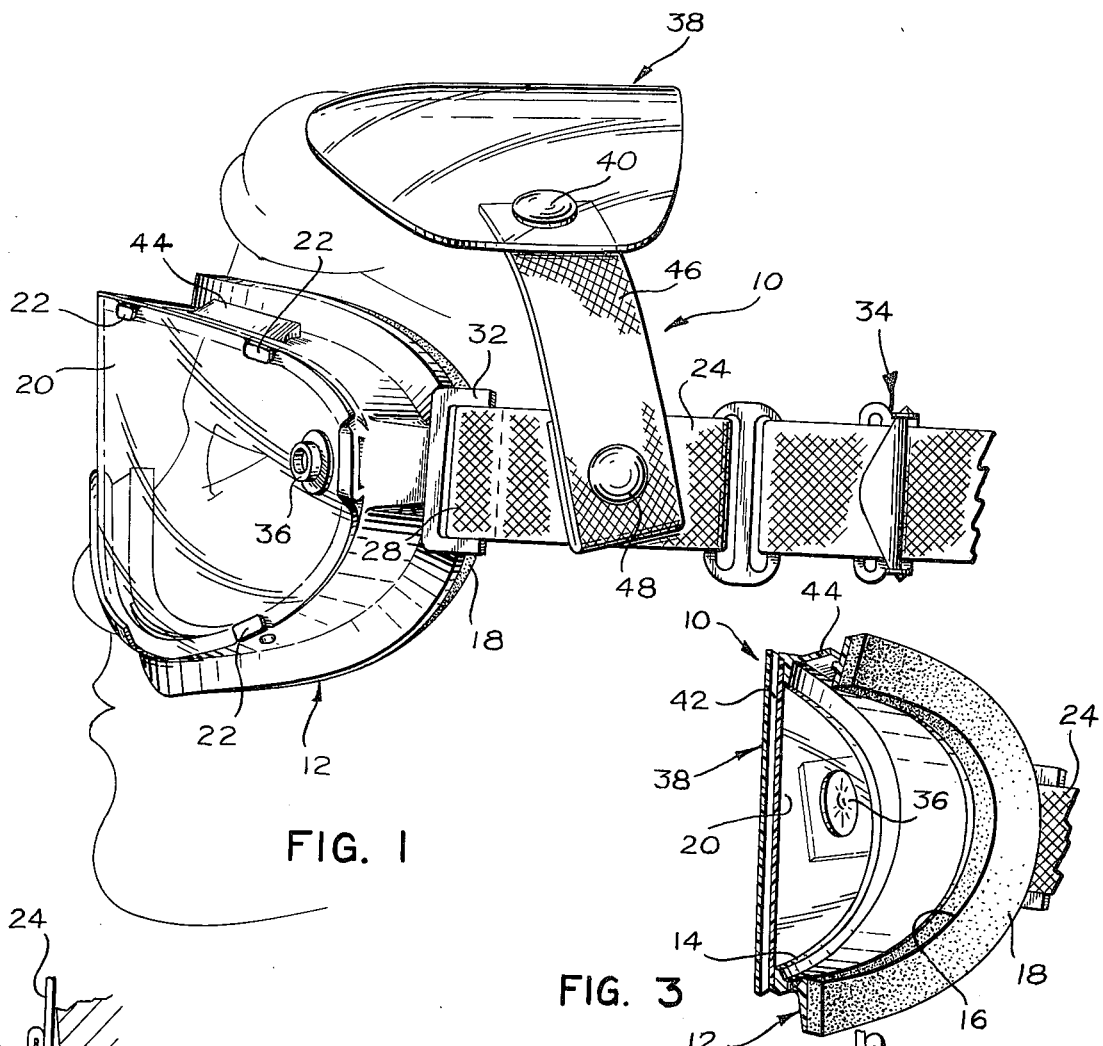
FIG. 1
FIG. 3
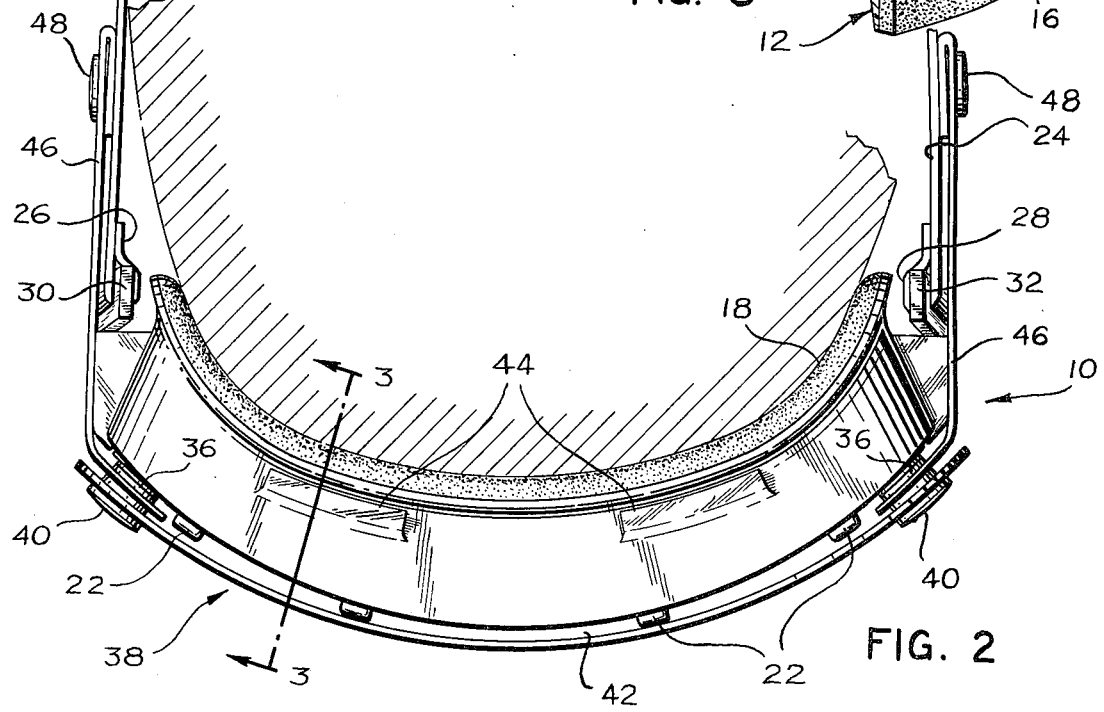
FIG. 2

DOUBLE LENS GOGGLE

BACKGROUND OF THE INVENTION

1. Field of the Invention

This invention relates to double lens goggles in general and more particularly to sports goggles.

2. Description of the Prior Art

Double lens goggles, especially of the sports type, have popularly served to reduce lens fogging in cold weather and/or offer the user a selection of clear or minimally subdued vision with one lens only or substantial subduction of the intensity or glare of light reaching the eyes with the addition of an auxiliary lens placed forwardly or rearwardly of the goggle main lens.

The former has been at least partially accomplished by spacing the auxiliary lens slightly away from the main goggle lens to form a thermal barrier keeping the innermost lens at a higher temperature than the outermost lens.

The latter, i.e. modification of the light reaching a wearer's eyes, has been accomplished through the provision of light filtering colored and/or polarized auxiliary lenses.

In all such cases, however, the auxiliary lens has been problematic in heretofore having to be completely removed from the goggle system and separately stored when not in use.

This removal of the lens, its handling for storage and the reverse process, together with the all too often improper storage (e.g. loosely in pockets of clothing) exposes the lens to excessive scratching and the abuse of crushing, not to mention the awkwardness imposed upon the user of handling the lens with gloved hands or removing gloves in cold weather and an attendant likelihood of loss or misplacement causing non-availability at times of need.

The present invention overcomes the aforesaid and related problems or drqwbacks of prior art double lens goggles and is particularly applicable to goggles used for protection of the eyes in various or variable lighting and weather conditions, especially during cold weather sports activities such as skiing or toboganning and the like.

SUMMARY OF THE INVENTION

The invention provides a goggle system comprised of a facepiece having a main lens, an elastic headband, auxiliary lens and elasticized pivotable attachment means for the auxiliary lens. These parts are readily detachable from each other for replacement or repair purposes but are normally kept interconnected as a single unit at all times during use or nonuse of the goggle.

The auxiliary lens attachment means is pivotally connected to the headband and, being elastic, is compliant with stretching and recovery of the headband thereby not interfering with the fit of the goggle system upon a wearer. The elasticity of this attachment means also allows the auxiliary lens to be freely pivoted away from the main lens of the goggle upwardly over various thickness and shapes of helmets or other headgear or downwardly under the chin without disruption of the fit of the main goggle structure before the eyes. The elastic nature of the auxiliary lens attachment means still further functions to draw this lens snugly against the head or helmet of a wearer preventing the annoyance of slippage from a desired position of non-use above or below the main lens.

The invention will be more fully understood by a reference to the following detailed description when taken in conjunction with the accompanying drawings.

IN THE DRAWINGS

FIG. 1 is a side elevational view of a preferred embodiment of the invention with its auxiliary lens shown in a position of non-use;

FIG. 2 is a top plan view of the goggle system showing the auxiliary lens in a position of use forwardly of the main goggle lens; and FIG. 3 is a cross-sectional view taken generally along line 3—3 of FIG. 2.

DESCRIPTION OF THE PREFERRED EMBODIMENTS

Referring more particularly to the drawings, it will be seen that goggle system 10 includes a facepiece 12 having a forwardly disposed ocular opening 14 (FIG. 3) and a rearwardly disposed facial opening 16 (FIG. 3). Facial opening 16 is provided with a peripheral cushion 18 formed of a foamed rubber or plastic which provides a substantially airtight seal and comfortable fit against the face when the goggle system is in use.

A main goggle lens 20 (FIGS. 1 and 2) is fixedly secured in the rim of the ocular opening of facepiece 12 by tabs 22 which are extensions of the material of facepiece 12.

Facepiece 12 is held in place against the wearer's face by elastic headbband 24. While being partially broken away in the present drawings for ease of illustration, headband 24 normally extends completely about the back of the head of a wearer, its opposite ends 26 and 28 (FIG. 2) being attached to corresponding connecting buckles 30 and 32 which are integral with facepiece 12. Sliding buckle 34 allows headband 24 to be adjusted in overall length between its ends 26 and 28 according to the wearer's head size. Once so adjusted, the goggle system can be removed and replaced upon the same wearer's head with the elasticity of headband 24 functioning to permit easy removal and replacement while holding facepiece 12 snugly in place during use. Headband 24 is preferably formed of woven elasticized strands or thread but may, alternatively comprise a length of extruded, cast or molded synthetic rubber or an equivalent thereof.

Main goggle lens 20 is provided with one component 36 of a snap fastener adjacent each of its opposite ends (FIGS. 1 and 3) and auxiliary lens 38, preferably of substantially the same size and shape as main lens 20, is provided with the second, preferably female, component 40 of each snap fastener adjacent each of its opposite ends.

Thus, by interengaging corresponding components 40 and 36 of each snap fastener, auxiliary lens 38 may be attached to goggle system 10 immediately forwardly of main lens 20 and slightly spaced therefrom as shown in FIGS. 2 and 3 to provide a thermal barrier space 42. Insulating air in space 42 keeps main lens 20 somewhat warmer than auxiliary lens 38 in cold environments thereby reducing fogging of the goggle system lenses. Also, but forming no particular part of the present invention, facepiece 12 may be louvered as at 44 and-/or perforated or otherwise vented to provide for a change of air in the space between the wearer's face and main lens 20 thereby keeping the humidity within the goggle facepiece at approximately the outside humidity and reducing the tendency for fogging from perspiration.

According to a particular feature of the present invention, auxiliary lens 38 which may be colored and/or light polarizing for subduction of glare and/or the intensity of light reaching a wearer's eyes, is elastically pivotally harnessed to the goggle system 10. Thus, lens 38 may be released (unsnapped) from main lens 20 and moved above or below facepiece 12 to a position of storage snugly against the head or headgear of a wearer.

The auxiliary lens attachment means comprises elastic straps 46 each having one of its ends fixed to lens 38 by a snap component 40 and releasably pivotally connected to headband 24 by a snap fastener 48. Straps 46 are free to pivot about the respective axes of fasteners 48 during manual adjustment of lens 38 to and away from such positions as forwardly of and above or below main lens 20 of goggle system 10.

With auxiliary lens 38 placed for storage above facepiece 12 against the head or headgear of a wearer as shown in FIG. 1, for example, or beneath the chin of the wearer (not shown) elastic straps 46 apply a tensioning force upon lens 38 preventing the annoyance of its slippage or misplacement from the desired position of storage during nonuse. The elasticity of straps 46 permits lifting of lens 38 away from a position of such storage and swinging into a position for attachment to main lens 20 and vice versa without interferring with the fit of facepiece 12 or the function of headband 24 in maintaining the previously mentioned snugness of facepiece fit.

While various parts of the goggle system 10 (e.g. auxiliary lens 38, main lens 20 and facepiece 12) may be readily detached from each other for replacement or repair purposes by releasing snap fasteners 48 and tabs 22, the system 10 as illustrated in the drawings is normally kept intact as a single unit at all times during use or non-use thereby eliminating the need for separate storage of parts, excessive awkwardness in handling of separate parts with or without gloved hands in cold weather and the likelihood of loss or misplacement of auxiliary lens 38.

I claim:

1. In a goggle system including a facepiece having a forwardly disposed main goggle lens and an elastic headband connected to opposite sides of said facepiece for supporting the whole goggle system upon the head of a wearer, the improvement of an auxiliary lens adapted to be used forwardly of said main goggle lens in combination with attachment means therefor comprising:
    a pair of elastic straps, one end of each strap being attached to said auxiliary lens adjacent one of each of its opposite sides;
    pivotable fastening means connecting the opposite ends of said straps directly to said headband at points one adjacent to each of said opposite sides of said facepiece; and
    said elastic straps being compliant with stretching and retraction of said elastic headband whereby interference with the function of said headband is avoided and said straps further being independently stretchable whereby said auxiliary lens is permitted to be selectively moved forwardly of said main goggle lens and swung about said pivotable fastening means from a position of use forwardly of said main lens to positions of storage above and below said facepiece all without disconnection from said elastic headband.

2. The goggle system according to claim 1 wherein said auxiliary lens is of approximately the same shape and size as said main goggle lens and includes fastening means for releasably attaching same to said main goggle lens.

3. The goggle system according to claim 2 wherein said fastening means comprises one snap fastener component secured to each of opposite sides of said main goggle lens and a mating snap fastener component secured to each of opposite sides of said auxiliary lens.

4. a goggle system according to claim 3 wherein said fastener components secured to said auxiliary lens further each comprise attachment means for said one end of each of said straps of said auxiliary lens attachment means.

5. A goggle system according to claim 1 wherein said pivotable fastening means connecting ends of said straps to said headband each comprise a dual component snap fastener, one component being pivotable about the other when the two are interengaged.

* * * * *